United States Patent
Befahy et al.

(10) Patent No.: US 10,898,715 B2
(45) Date of Patent: Jan. 26, 2021

(54) IMPLANTABLE PROBE COMPRISING A SLEEVE, PARTICULARLY FOR THE STIMULATION OF A NERVE, AND MANUFACTURING METHOD FOR SAID SLEEVE

(71) Applicant: SORIN CRM SAS, Clamart (FR)

(72) Inventors: Stéphane Befahy, Brussels (BE); Hervé Mevel, Chastre (BE); Vincent Callegari, Corbais (BE)

(73) Assignee: Sorin CRM SAS, Clamart (FR)

( * ) Notice: Subject to any disclaimer, the term of this patent is extended or adjusted under 35 U.S.C. 154(b) by 215 days.

(21) Appl. No.: 16/062,610

(22) PCT Filed: Dec. 12, 2016

(86) PCT No.: PCT/EP2016/080683
§ 371 (c)(1),
(2) Date: Nov. 14, 2018

(87) PCT Pub. No.: WO2017/102662
PCT Pub. Date: Jun. 22, 2017

(65) Prior Publication Data
US 2019/0076650 A1    Mar. 14, 2019

(30) Foreign Application Priority Data

Dec. 18, 2015   (FR) ...................................... 15 62848
Dec. 18, 2015   (FR) ...................................... 15 62853

(51) Int. Cl.
*A61N 1/36*   (2006.01)
*A61N 1/05*   (2006.01)

(52) U.S. Cl.
CPC ....... *A61N 1/36053* (2013.01); *A61N 1/0551* (2013.01); *A61N 1/0556* (2013.01);
(Continued)

(58) Field of Classification Search
CPC .............. A61N 1/36053; A61N 1/0551; A61N 1/0556; A61N 1/36064; A61N 1/36078; A61N 1/36085
(Continued)

(56) References Cited

U.S. PATENT DOCUMENTS

| | | | |
|---|---|---|---|
| 4,602,624 A | 7/1986 | Naples | |
| 5,251,634 A | 10/1993 | Weinberg | |

(Continued)

FOREIGN PATENT DOCUMENTS

| | | |
|---|---|---|
| EP | 2 959 938 A1 | 12/2015 |
| WO | WO 2014/106023 A1 | 7/2014 |

OTHER PUBLICATIONS

French Search Report on French Patent Application No. 1562848 dated Aug. 10, 2016. 9 pages.
(Continued)

*Primary Examiner* — Erin M Piateski
(74) *Attorney, Agent, or Firm* — Foley & Lardner LLP

(57) ABSTRACT

The present invention relates to an implantable probe comprising a sleeve adapted to be wound around an elongated cylindrical organ, such as a vagus nerve. The sleeve comprises a sheet of elastically deformable material carrying a detection/stimulation electrode being prestressed so as to allow its self-winding from an initial position where the sheet is held under stress in the deployed state to a final position where the sheet is freely spirally wound forming a sleeve around the organ. The sheet is delimited by inner and outer lateral edges of the sleeve after winding, a first transverse edge joining the first homologous ends of the first lateral edge and the second lateral edge, and a second opposite transversal edge joining homologous second ends of the first lateral edge and the second lateral edge. In the final position of the sleeve, the sheet comprises at least one
(Continued)

area having a constraint near the first and/or second transverse edge.

12 Claims, 3 Drawing Sheets

(52) U.S. Cl.
CPC ...... *A61N 1/36064* (2013.01); *A61N 1/36078* (2013.01); *A61N 1/36085* (2013.01)

(58) Field of Classification Search
USPC ........................................................ 607/118
See application file for complete search history.

(56) References Cited

U.S. PATENT DOCUMENTS

| | | | |
|---|---|---|---|
| 2008/0004673 A1* | 1/2008 | Rossing | A61N 1/05 607/44 |
| 2014/0188202 A1* | 7/2014 | Zarembo | A61N 1/0556 607/118 |

OTHER PUBLICATIONS

International Search Report and Written Opinion on International Patent Application No. PCT/EP2016/080683 dated Mar. 13, 2017. 11 pages.

* cited by examiner

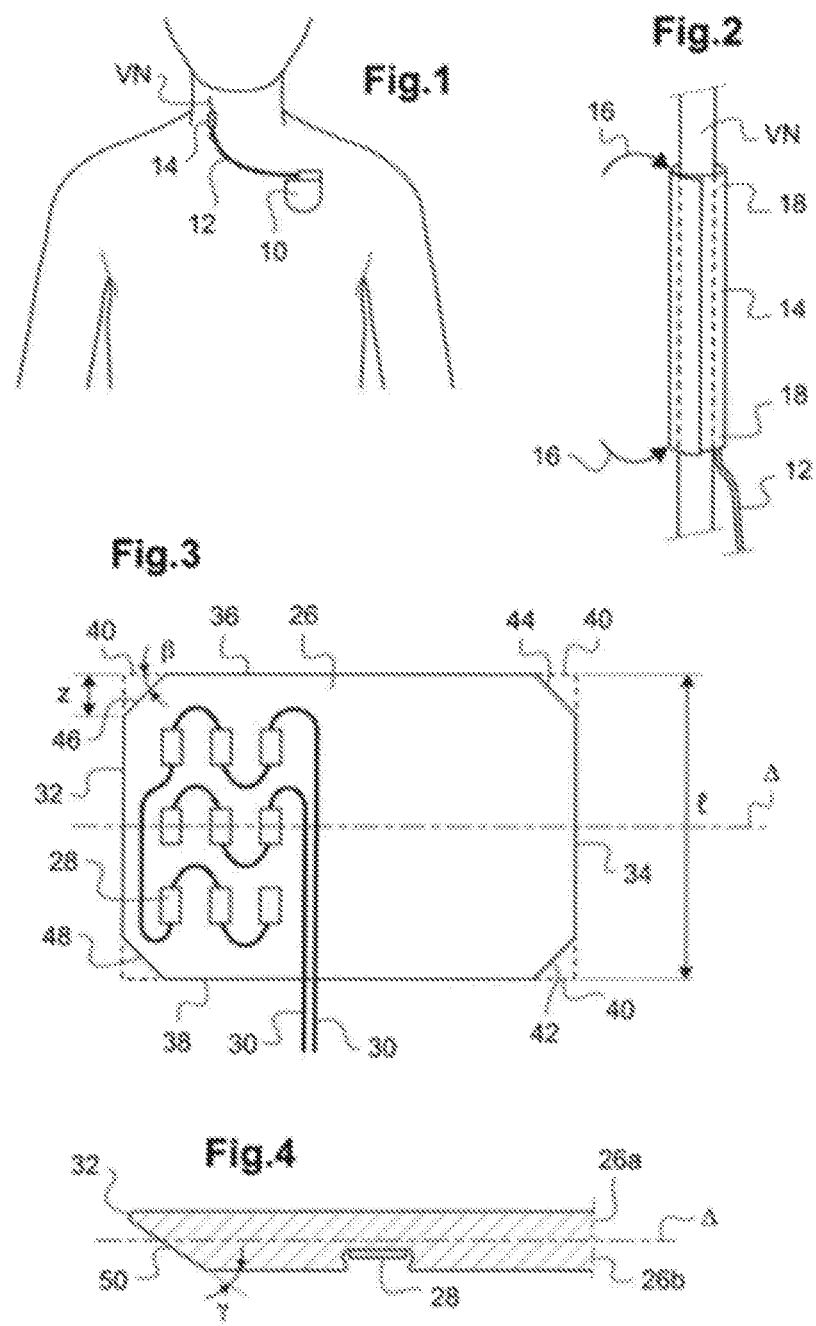

IMPLANTABLE PROBE COMPRISING A SLEEVE, PARTICULARLY FOR THE STIMULATION OF A NERVE, AND MANUFACTURING METHOD FOR SAID SLEEVE

CROSS-REFERENCE TO RELATED PATENT APPLICATIONS

This application is a 371 U.S. National Application of International Application No. PCT/EP2016/080683, filed Dec. 12, 2016, which claims the benefit of and priority to French Patent Application No. 1562848, filed Dec. 18, 2015 and French Patent Application No. 1562853, filed Dec. 18, 2018, both of which are incorporated herein by reference in their entirety.

BACKGROUND

The invention relates to "active implantable medical devices" as defined by Directive 90/385/EEC of 20 Jun. 1990 the Council of the European Communities, specifically to implants that allow stimulation of an elongated cylindrical organ and/or the collection of electrical potentials on such an organ.

The invention more particularly relates to the stimulation of the nerves, especially the stimulation of the vagus nerve in the case of therapies referred to as VNS (Vagus Nerve Stimulation).

However, this application has no restrictive character, and the invention may be used to detect/stimulate any other organ, or for other purposes such as the local delivery of an active agent, etc., to this organ, as long as the target organ has an elongated cylindrical shape.

The stimulation of the nervous system is a therapy recognized regarding many disorders such as epilepsy, pain, heart failure, apnea, obesity, etc.

The devices used to this end comprise a probe provided with an electrode implanted on the vagus nerve and a generator delivering electric pulses to said electrode.

VNS therapy is designed to generate bursts of repetitive pulses, synchronized or not on the heart rate depending on the condition that is desired to treat, these pulses being superimposed on signals that are naturally conveyed by the nervous system, organized in a closed loop. The stimulation of the vagus nerve may act by efference, directly to an organ, or by afference, towards the brain to influence the central nervous system: the arbitrary signal consisting of the VNS pulses will then be interpreted by the central nervous system as a constraint that said central nervous system will attempt to compensate to oppose it and thereby prevent the expected effects to happen.

The invention more particularly relates to the implanted device at the electrode/nerve interface, which enables to keep the electrodes in contact with the nerve or in the close vicinity thereof.

Given the elongated and approximately cylindrical configuration of a peripheral nerve such as the vagus nerve, the most commonly used device is in the form of a tubular sleeve, wound around the nerve. The sleeve is generally made of an elastomer such as silicone, due to the excellent biocompatibility of this material, and it carries on its inner face, applied against the nerve, the stimulation (and/or detection) electrodes.

Such a sleeve is for example disclosed in U.S. Pat. No. 4,602,624 A. The sleeve disclosed herein is made from two elastomer sheets laminated together, one of them having been previously stretched in a preferred prestressing direction. The resulting composite sheet is then cut to give a rectangular part which, due to the prestressing of one of the sheets, will naturally tend, in a free state, to be spirally self-wound around an axis that is perpendicular to the prestressing direction (a "spiral" being a plane curve winding regularly around a point from which it deviates more and more from).

Compared to a rigid sleeve, the sleeve described in this document has the advantage of simplicity of implementation: the surgeon only needs to unwind it, pass it under the nerve and release it so it winds itself around the nerve. In addition, the sleeve is self-adaptable: indeed, immediately after the implantation, a normal inflammatory process produces a temporary swelling of the nerve, which then disappears. If one chooses a flexible spiral sleeve with an inner diameter at rest slightly smaller than the diameter of the nerve, this sleeve—with its electrodes—would always remain tightly pressed against the nerve even if the diameter thereof varies, and without risk of excessive pressure that might damage nerve tissues irreversibly.

However, this device is not without drawbacks.

A first drawback occurs during the implementation: to put the sleeve in place, once the target nerve is reached, the surgeon pulls the nerve out of the incision he did, so he can slide the unwound sleeve held in the chosen location. During this maneuver, the traction exerted on the nerve can imply locally, at the ends of the sleeve, relatively high stresses on the nerve tissue, that may be damaged. Another possible cause of nerve damages is the procedure's duration, which may expose the nerve to air for too long. It is therefore necessary for the sleeve's implantation procedure to be very brief, limiting as much as possible manipulations of the nerve. Still during implantation, the corners of the sleeve tend to wind themselves and interfere with implantation, which complicates the task of the surgeon.

A second drawback, which appears after implantation, is that the innermost edge of the sleeve, that is to say the edge wound around the nerve, rests against the latter and exerts pressure, along the contact line, that tends to stress or even distort, the nerve, with potentially deleterious effects. The stiffness of the sleeves can also lead to unacceptable shearing forces at their ends. A further risk is that, upon implantation, the surgeon allowed the portion of the outer edge of the sleeve to wind itself in the opposite direction, which then forms a second turn in the opposite direction from the first. The radius of curvature is thus no longer the one it was supposed to be, resulting in an allowance risk.

A third drawback is related to the manufacturing process. As above mentioned, the sleeve is achieved by laminating together two elastomer sheets, with a directional prestressing applied to one of them. These sheets being very thin (their typical thickness is around 100 µm), problems of homogeneity of the material and of thickness tolerance may appear on the extent of the surface of a single sheet as well as between two sheets, which limits the reproducibility of the sleeves production's process. It is possible to overcome this disadvantage by using large sheets, but with a negative impact on the industrial process. It is also possible to use thicker, more controllable sheets during the process, but with an increased risk of damage to the nerve due to a diminished flexibility and therefore a lesser ability of the sleeve to comply with the nerve's morphology in the implantation area.

Finally, a fourth drawback lies in the fact that insulating material is used as a support for the electrodes and for the blunt termination of the sleeve's ends, resulting in the creation of virtual electrodes of anode or cathode type, responsible for unwanted blocking or stimulating effects.

A sleeve for an implantable probe composed of a plurality of propellers is also known from U.S. Pat. No. 5,251,634 A. A pair of electrically conductive straps is respectively incorporated into the material of two propellers. Other propellers forming the sleeve are used to hold the sleeve on the nerve.

This technical solution also has several disadvantages. In particular, implantation of such a device having a plurality of propellers is difficult to make around the nerve. In addition, stimulation currents to be applied to the nerve are not applied only on the latter since no continuous protection of this sleeve is provided. Finally, a sleeve having propellers is not adapted to receive the electrodes which must have more contact points, in particular for tripolar stimulation.

Other sleeves for an implantable probe were also designed, in particular of cylindrical shape with a longitudinal opening allowing the implantation of the sleeve around the nerve. Different sleeve locking systems were then designed. However, these sleeves are of fixed diameter, and so as not to damage the nerve during implantation of the sleeve, the latter should be chosen larger than the diameter of the nerve. A good connection between the sleeve and the nerve is not possible and therefore the electrodes are kept in contact with the nerve.

The need therefore remains for a thin elastomer self-windable sleeve that can be produced by an effective industrial process, with a high degree of reproducibility while suppressing the known side effects of existing sleeves.

SUMMARY

The object of the invention is to solve these problems by proposing a new self-windable spiral sleeve structure:
  facilitating rapid implantation by the surgeon, without introducing excessive stresses on the nerve, which in particular avoids causing a shearing force on the edges of the sleeve;
  that respects the anatomic integrity of the nerve after implantation while still providing a satisfactory holding of the sleeve to the chosen implantation site;
  which can be produced by an optimized method from the industrial constraints standpoint; and
  eliminating the generation of virtual electrodes.

To this end, the invention provides an implantable probe comprising a self-windable sleeve as described in particular by the aforesaid U.S. Pat. No. 4,602,624 A, that is to say comprising, in a known manner by itself, a sleeve adapted to be wound around an elongated cylindrical organ such as a nerve and comprising a sheet of elastically deformable material having at least one detection/stimulation electrode. The sheet is prestressed so as to allow its self-winding, from an initial position where the sheet is held under stress in the deployed state to a final position where the sheet is freely spirally wound forming a sleeve around the organ. The sheet is delimited by an outer lateral edge of the sleeve after winding, an inner lateral edge of the sleeve after winding, and a first transverse edge joining the first homologous ends of the first and the second lateral edge, and a second opposite transversal edge joining homologous second ends to the first lateral edge and the second lateral edge.

According to the invention, in the sleeve's final position, the sheet comprises at least one area having a constraint near the first and/or second transverse edge on the longitudinal edges lower than the constraint of an area located in a middle region of the sheet so as to create at least one end of the flared sheet.

According to various advantageous subsidiary characteristics:
  the area having a smaller constraint is localized in at least one area extending up to 50% of the width of the sheet near the first and/or second transverse edge, the width of the sheet being defined by the distance between the first and the second transverse edge;
  the lowest constraint area exhibits a decreasing constraint gradient across the width of the area, extending from the inside of the sleeve towards the transverse edge of the sleeve;
  the area having a lower constraint is formed of an elastomer sheet and the area in the middle area comprises at least two elastomer sheets; and/or
  the lowest constraint area exhibits a decreasing constraint gradient across the width of the area extending from the inside of the sleeve towards the transverse edge of the sleeve.

The invention also relates to a manufacturing method of a sleeve for an implantable probe, adapted to be wind around an elongated cylindrical organ such as a nerve, this sleeve comprising a sheet of elastically deformable material carrying at least one detection/stimulation electrode, the sheet being prestressed so as to allow its self-winding from an initial position where the sheet is held under stress in the deployed state to a final position where the sheet is freely spirally wound forming a sleeve around the organ, the sheet being delimited by an outer lateral edge of the sleeve after winding, an inner lateral edge of the sleeve after winding, and a first transverse edge joining first homologous ends to the first lateral edge and the second lateral edge, and a second opposite transversal edge joining second homologous ends of the first lateral edge and the second lateral edge, the sheet being formed of at least a first and a second elastomer sheet.

In a first embodiment, the method comprises a stretching step of the second elastomer sheet in a direction that is perpendicular to the winding axis of the sheet, a lower stretching being performed in an area near the first and/or second transverse edge on the longitudinal edges with respect to a prestressed area located in a middle region of the sheet, and a fixing step of the second elastomer sheet stretched over the first elastomer sheet.

Preferably, the area having a lower constraint is localized in at least one area extending up to 30% of width of the elastomer sheet near the first and/or second transverse edge, the width of the elastomer sheet being defined by the distance between the first and the second transverse edge of the sheet.

Advantageously, the lower constraint region exhibits a decreasing constraint gradient across the width of the area extending from the end of the area closest to the middle part of the elastomer sheet to the transverse edge of the lower prestressed area.

In a second embodiment, the method comprises a stretching step of the second elastomer sheet in a direction that is perpendicular to the axis of winding of the sheet, a fixing step of the second elastomer sheet stretched over the first elastomer sheet, the first elastomer sheet and the second elastomer sheet being of different widths, the width being defined by the distance between the lateral edges of said elastomer sheets.

According to various advantageous subsidiary characteristics:
  the fixing step consists in fixing the elastomer sheet of smaller width substantially centered over the width of the widest elastomer sheet;

the elastomer sheet of smaller width has a width between 60 and 80% of the width of the other elastomer sheet;

the width of the first elastomer sheet is lower than the width of the second elastomer sheet; and/or the width of the second elastomer sheet is lower than the width of the first elastomer sheet.

BRIEF DESCRIPTION OF THE DRAWINGS

We will now describe an exemplary embodiment of the present invention, with reference to the accompanying drawings wherein the same references are used from one figure to another for identical or functionally similar elements.

FIG. 1 is a general view for presenting a VNS stimulation assembly, showing the generator and the vagus nerve as well as the probe used.

FIG. 2 is a view of a sleeve according to the prior art, wound around the vagus nerve during the implementation procedure.

FIG. 3 is a plan view of the sleeve according to the invention, in an unwound configuration which is that of the sleeve at the time of its fabrication.

FIG. 4 is a sectional view along the thickness direction of the sleeve of FIG. 3, in a partial view in the region of one edge, in particular showing the two-layered structure laminated together.

DETAILED DESCRIPTION

Figure 5:
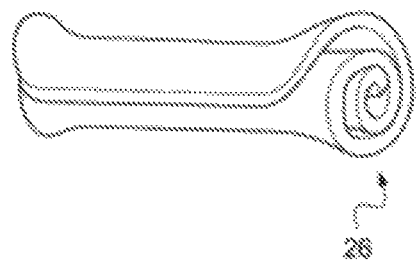
FIG. 5 is a perspective view of the sleeve of FIG. 3 in its open configuration, wound on itself in accordance with the invention.

We will now describe an exemplary embodiment of a probe of vagus nerve stimulation according to the invention, this example being in no way limiting as said in the introduction.

In FIG. 1, reference 10 designates the housing of a VNS stimulation implantable generator. The generated stimulation pulses are delivered by a probe 12 carrying at its distal portion a sleeve 14 provided with electrodes near the vagus nerve VN and prone to stimulate the latter by the bursts of pulses produced by the generator 10.

FIG. 2 is a view of a sleeve 14 according to the prior art, wound around the vagus nerve VN during the implantation procedure.

To place the sleeve, the surgeon had to isolate the vagus nerve VN, to be able to slide therein the sleeve held in the chosen location. After spirally self-winding, the sleeve 14 is as shown in FIG. 2. In this particular configuration, stresses are exerted by the cylindrical sleeve in the region 16 due to the discontinuity in rigidity between the part of the nerve enclosed within the sleeve 14 and the free end portion beyond the sleeve. This discontinuity between a portion where the nerve is locked and one in which it is free locally creates stresses at the point of transition, stresses which may damage the nervous tissue.

Another drawback, also specific to the sleeves of the prior art, lies in that if one considers the innermost end of the spirally wound sleeve 20, the fact that this end is sandwiched by the remainder of the sleeve has for consequences to exert stresses on the nerve VN in the region 22 located in the vicinity of this end (stresses schematised by the arrows 24) which have the effect of deforming the nerve permanently, with potentially deleterious effects.

Another drawback is linked to the creation of virtual electrodes as explained below.

The neural stimulation is an artificial activation of the nerve fiber, activation being a mild electrical stimulation, in particular by applying a short pulse of electric current on the membrane of the nerve fiber, called the action potential.

However, the inside of the nerve membrane is not accessible and the current through the membrane must be obtained by application of an external potential field.

Ohm's and Kirchhoff's laws indicate that the current entering the membrane (Im) is defined as follows:

$$Im = d(\sigma z \cdot d(Uz))/dz^2,$$

z being the diameter of the nerve,

σz being the electrical conductivity along the axis of the nerve, and

Uz being the potential applied to the membrane.

The outer membrane current activates the membrane by depolarization while the inner membrane current inhibits the activation or the propagation of the action potentials by hyperpolarization.

The electrode support material, in general a silicone elastomer, has a very low conductivity compared to fluids and biological tissues surrounding the sleeve.

Thus, the current generated by the electrodes along the nerve will encounter a sudden change in conductivity of the material (σz) at both ends of the sleeve. This results in generation of internal currents corresponding to an anode type virtual electrode, or outer currents corresponding to a cathode type virtual electrode through the membrane. These virtual electrodes can stimulate the nerve or in contrast block the transmission of an action potential. These effects are in most cases a nuisance because they cannot be controlled.

Another drawback of this device of the prior art is due to the fact that the virtual anodes and cathodes do not act only on the nerve, but also on the environment of the sleeve surrounding the nerve, namely, muscles, skin or other nerves leading to side effects for the patient.

Finally, such a sleeve having a specific rigidity, in particular on the edges of the sleeve, may damage the nerve by creating a pressure on the nerve, that can stress and deform the nerve. Furthermore, the edges of the sleeve can exert shearing forces on the nerve. These various drawbacks, as well as those exposed in the introduction, can be solved by a sleeve constructed according to the teachings of the invention, shown in FIGS. 3 to 7.

FIG. 3 is a plan view of the sleeve according to the invention, in an unwound configuration which is that of the sleeve at the time of fabrication, i.e. in an initial position where the sheet forming the sleeve is held under stress in the deployed state and FIG. 5 is a view of the sleeve according to the invention in its wound configuration, i.e. in a final position where the sheet forming the sleeve is freely spirally wound, especially around the NV nerve, presenting flared ends in order to minimize any constraint in the region between the part of the nerve enclosed within the sleeve 26 and the free part of the nerve beyond the sleeve.

The sleeve 26 according to the invention comprises a sheet 26 made of elastically deformable material. The sheet 26 is made in particular from two elastomer sheets 26a and 26b (FIG. 4) secured together, for example with silicone.

According to one embodiment, one of the elastomer sheets 26a and 26b is subjected beforehand to its assembly with the other elastomer sheet to a stretching prestressing along the direction Δ, which, in this example, is the direction of greatest dimension of the sheet 26.

As explained in the U.S. Pat. No. 4,602,624 A abovementioned, this technique allows to make the sleeve spirally self-wound when the sheet 26, after manufacture of the sleeve, is no longer subjected to any external constraint, resulting to the wound configuration. In this way, the sheet 26 is prestressed so as to allow its self-winding from an initial position where the sheet is held under stress in the deployed state to a final position where the sheet is freely spirally wound forming a sleeve around the organ.

According to another embodiment, the two elastomer sheets 26a and 26b are subjected, prior to their assembly, to a stretching prestressing in the direction Δ, which is, in this example, the direction of greatest dimension of the sheet 26. However, one of the elastomer sheets is subjected to a greater stretching prestressing than the other elastomer sheet.

The silicone is preferably chosen as the base material for the implantable sleeve, due to its excellent biocompatibility properties, both in terms of bio-tolerance (the implant does not cause damage to the host: absence of toxicity and mechanical damage of the tissues) and biostability (the implant withstands conditions induced by the host).

According to the invention, to create at least one end of the sleeve in a flared shape, the sheet 26 in the deployed initial position, comprises at least one area of lower prestressing near the first and/or second transverse edge on the longitudinal edges with regards to a prestressing area located in a middle region of the sheet so as to create at least one flared end when the sheet is freely spirally wound.

In the final position of the sleeve, i.e. wound, the sheet comprises at least one area having a constraint near the first and/or second transverse edge on the longitudinal edges lower than the constraint of an area situated in a middle region of the sheet so as to create at least one flared end when the sheet is freely spirally wound.

Thus, when the sleeve is wound, the area having a lower constraint has a diameter greater than the diameter of the area having a higher constraint, in particular located in the middle region of the sleeve.

According to a particular embodiment, the sheet 26 carries, in the region intended to come into contact with the vagus nerve after winding (the region on the left in FIG. 3), a number of electrodes 28 brought in surface of the sheet or embedded in the thickness of the elastomer material.

Alternatively, the electrodes 28 are positioned between the two elastomer sheets 26a and 26b. The elastomer sheet in contact with the vagus nerve after winding may then comprise through- or blind openings, at the electrodes.

These electrodes 28 are connected to wires 30 intended to be connected to the pulse generator 10. In the example illustrated in FIG. 3, these electrodes 28 are distributed in a uniform manner along the axis of winding of sleeve 26 and are interconnected so as to constitute a matrix of quasi-tripole-type contacts (anode/cathode/anode or vice versa) connected to the corresponding micro-cables 30.

To achieve the sleeve of the invention, it is possible to use relatively thin sheets (of the order of 100 microns), which results in very flexible sleeves, and therefore very well tolerated, without compromising ease of installation and with a very gradual transition between the nerve and the sleeve.

The sleeve is made from the sheet 26 which has a rectangular shape, with an inner lateral edge 32 forming a first width (which will come within the spiral after winding of the sleeve), a second opposite lateral edge 34 forming a second width (which will come outside the sleeve after winding), and a first transverse edge 36 joining homologous first ends to the first lateral edge 32 and the second lateral edge 34, and a second opposite transverse edge 38 joining homologous second ends of the first lateral edge 32 and second lateral edge 34.

As illustrated in FIG. 3, the right-angled corners of the rectangular sheet can be cut (by stamping, cutting with a blade or any other suitable manufacturing process) so as to eliminate the regions delimited by the dashes 40, thereby forming bevelled edges 42, 44, 46, 48. These bevels for example form an angle β from 30° to 60° and extend over a width z of 10 to 25% of the total width ι of the sheet 26.

Alternatively, the right-angled corners of the rectangular sheet may be rounded.

Furthermore, in the thickness direction, the end 32 may have a chamfered edge 50, the chamfer being turned toward the face of the sheet to be applied against the nerve. This chamfer is inclined at an angle γ between 20° and 45°, for example.

According to the invention, the sheet 26, in the freely spirally wound position, comprises at least one area having a constraint near the first and/or second transverse edge 36, 38 on the longitudinal edges lower than the constraint of an area located in a middle region of the sheet so as to create one or two flared ends of the sleeve, as shown in FIG. 5.

The fact that a stress is higher in the middle portion of the sleeve relative to one or both longitudinal edges implies that the sleeve is firmly held on the nerve, and that the ends of the sleeve are more flexible than the middle portion. In this way, the flared ends of the sleeve when in the unwound position allow on one hand to avoid the creation of virtual electrodes and on the other hand, to create a nerve shear at the end of sleeve.

Indeed, the flared shape of the sleeve's ends allows to reduce the difference in conductivity at the sleeve's ends, which has the effect of eliminating the unwanted generation of virtual electrodes.

As shown in FIG. 5, the area of the sleeve's sheet having a smaller constraint is localized in at least one area extending up to 50% of the width of the sheet near the first and/or second transverse edge, the width of the sheet being defined by the distance between the first and the second transverse edge, in other words, the width corresponds to the height of the sleeve as shown in FIG. 5.

According to a particular embodiment, the lowest constraint area extends up to 30% of the width of the sheet near the first and/or second transverse edge in the final position of the sleeve, i.e. wound.

According to another particular embodiment, the lowest constraint area exhibits a decreasing constraint gradient across the width of the area extending from the inside of the sleeve towards the transverse edge of the sleeve, so that the constraints are lower in the periphery of the sleeve relative to the substantially middle portion of the sleeve.

Indeed, in order to create a gradually flared shape, the area of lower constraint is not formed over its entire width with the same force of constrain but, on the contrary, a difference in constraint is applied in a decreasing manner from the area near the middle portion of the sleeve to the other end of the area extending towards the transverse edge of the sheet 26 so as to create a constraint gradient on said area going from a higher constraint towards the middle part of the sleeve to go with a lower constraint at the sleeve's periphery.

Figure 7:
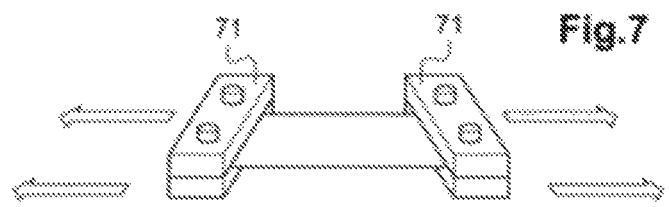
FIG. 7 is an illustration of stretching means of a sheet according to the invention.

This constraint gradient between substantially the middle portion of the sleeve and the sleeve's peripheral edge may be created by the use of stretching means 71 positioned at each end of the elastomer sheet in the stretching direction to be made (as shown in FIG. 7 detailed below).

According to an advantageous embodiment, the sheet 26 comprises two areas of lower constraint near the first and the second transverse edge so as to create two flared ends when the sheet is freely spirally wound as shown in FIG. 5.

Of course, the invention is applicable with one or two areas of lower constraint located on one or both transverse edges of the sheet so as to create a sleeve having one or both flare shaped ends.

Figure 6:
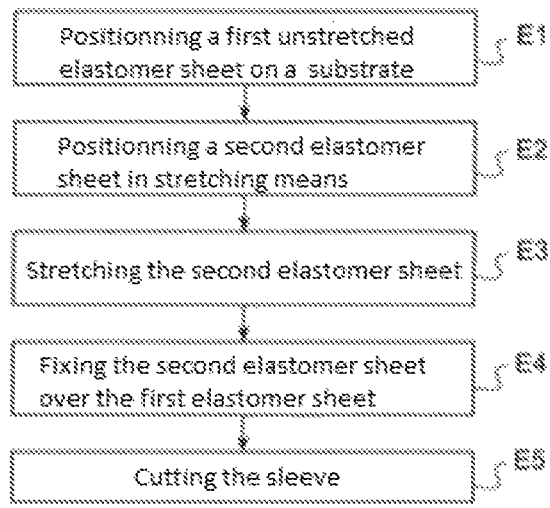
FIG. 6 is a manufacturing method of a sleeve according to the invention.
Figure 8:
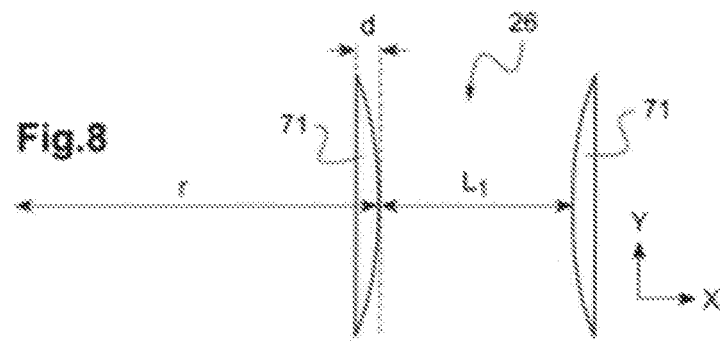
FIG. 8 illustrates curved stretching means of circular shape of the elastomer sheet side.

Referring to FIGS. 6 to 8, a manufacturing method of a sleeve for an implantable probe will now be described, according to the invention.

The manufacturing method, whose successive steps are shown schematically in FIG. 6, starts with an E1 step consisting in positioning a first unstretched elastomer sheet on a support.

Step E1 is followed by a step E2 consisting in positioning a second elastomer sheet in stretching means adapted to stretch the elastomer sheet in the longitudinal direction of the stretching to be made.

FIG. 7 illustrates the two stretching means 71 fixed to both ends of the second elastomer sheet to stretch.

According to the embodiment illustrated in FIG. 7, the stretching means 71 are of curved shape on the side of the sheet to create a decreasing stretching prestressing extending from the middle portion of the elastomer sheet's lateral edges to the elastomer sheet's transverse sides.

As shown in FIG. 8, the curved stretching means have a circular shape on the side of the elastomer sheet that has a radius r creating a distance d between the stretching positions in the middle portion of the sheet and at the transverse edges.

The distance d reduces the prestressing created on the transverse edges. Indeed, the prestressing performed at the middle portion of the elastomer sheet can be measured as follows:

$$(L_2-L_1)/L_1,$$

$L_1$ being the length of the sheet between the two stretching supports before stretching, the length being defined by the distance between the two stretching supports in the middle portion of the elastomer sheet and $L_2$ being the length of the sheet between the two stretching supports after stretching.

And the prestressing performed at the transverse edges of the elastomer sheet can be measured as follows:

$$(L_2-L_1)/(L_1+d),$$

$L_1$ being the length of the sheet between the two stretching supports before stretching, the length being defined by the distance between the two stretching supports, and $L_2$ being the length of the sheet between the two stretching supports after stretching.

According to an illustrative example of this embodiment, a sleeve according to the invention having flared ends may be achieved by having a prestressing during the manufacture of 70% along the axis X at the middle portion of the elastomer sheet, a radius of curvature r of the stretching means 71 between 160 and 60 mm, which has for consequences the creation of a distance d between 5 and 15 mm.

Step E2 is followed by a stretching step E3 of the second elastomer sheet in a direction Δ perpendicular to the winding axis of the sheet.

According to the invention, a lower stretch in an area near the first and/or second transverse edge in relation to a prestressing area located in a middle region of the sheet is performed.

Step E3 is then followed by step E4 for fixing the second elastomer sheet stretched over the first unstretched elastomer sheet. The fixation can be achieved for example by gluing.

According to a particular embodiment, the two elastomer sheets are stretched differently, i.e. the first elastomer sheet is stretched and the second elastomer sheet undergoes a higher stretching according to step E3.

Step E4 is followed by a cutting step E5 of the sleeve to the desired size, in particular a cutting along the axis X in order to define the length of the sheet forming the sleeve.

According to a particular embodiment, the lowest stretching area is located in at least a region extending up to 50% of the width of the elastomer sheet near the first and/or second transverse edge, the width of the elastomer sheet being defined by the distance between the first and the second transverse edge of the sheet 26. According to one particular embodiment, the lowest constraint area extends up to 20% of the width of the sheet near the first and/or second transverse edge.

The manufacturing method of an above-mentioned sleeve described further comprises a step of positioning a number of electrodes on the inner or outer face of one of the two elastomer sheets or within the thickness of one of the two elastomer sheets in the region intended to come into contact with the vagus nerve after winding. If the electrodes are positioned in such a way that they are not in contact with the nerve, then the method further comprises a step of through- or blind openings near the electrodes so as to improve the stimulation of the vagus nerve. The openings may be performed by punching or by laser cutting.

Figure 9:
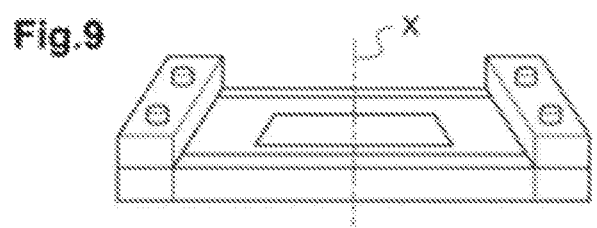
FIG. 9 illustrates a variant embodiment for obtaining a sheet having prestressing gradients according to the invention.
Figure 10:
FIG. 10 shows a sleeve formed of two elastomer sheets of different widths, for the variant of FIG. 9.
Figure 11:
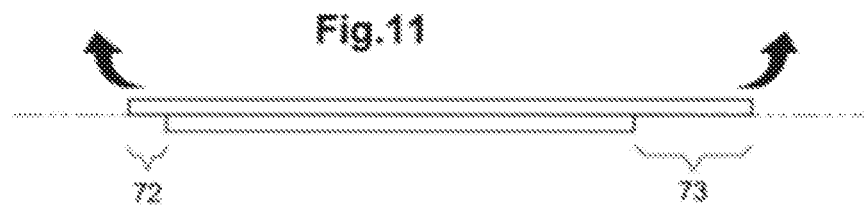
FIG. 11 shows a sleeve formed of two elastomer sheets of different widths that are not centered on their width, for the variant of FIG. 9.

FIGS. 9 to 11 illustrate an implementation variant of the above-mentioned manufacturing method.

Again, the sheet 26 preferably comprises two areas of lower constraint near the first and the second transverse edge so as to create two flared ends when the sheet is freely spirally wound as shown in FIG. 5.

As illustrated for example FIGS. 10 and 11, these areas of lower constrain areas are formed of a single elastomer sheet. Of course, the invention is applicable with one or two areas of lower constraint located on one or both transverse edges of the sheet so as to create a sleeve having one or both ends of flared shape.

FIG. 9 illustrates the assembly of the two elastomer sheets showing the difference in width of the two elastomer sheets. This difference in width allows the creation of a constraint gradient so as to obtain a sleeve as shown in FIG. 6. The axis X shown in FIG. 9 illustrates the winding axis of the resulting sheet.

As illustrated for example in FIGS. 10 and 11, to create at least one flared shaped end of the sleeve, the sheet 26 comprises at least one area formed from an elastomer sheet near the first and/or second transverse edge on the longitudinal edges and an area formed from the superimposition of two elastomer sheets 26a and 26b located in a middle region of the sheet, at least one of the superimposed elastomer sheet having undergone stretching prior to its assembly with the second elastomer sheet.

In this way, a constraint gradient difference creating the flared shape of the sleeve, shown in FIG. 5, is created at the junction between the area comprising an elastomer sheet and the area having two elastomer sheets.

Thus, the sleeve comprises in its end position, i.e. wound, at least one area consisting of a single elastomer sheet and a middle region composed of at least two elastomer sheets, the area or areas composed of an elastomer sheet having a constraint lower than the area consisting of two elastomer sheets. The transition from the area of the sheet 26 consisting of an elastomer sheet to the area of the sheet 26 consisting of two elastomer sheets creates a flared end when the sheet is freely spirally wound.

FIG. 10 illustrates an assembly of two elastomer sheets of different widths.

According to the invention, the first elastomer sheet and the second elastomer sheet are of different widths, the width being defined by the distance between the lateral edges of said elastomer sheets. In particular, the elastomer sheet of lower width has a width between 60 and 80% of the width of the other elastomer sheet.

Due to the difference in width of the two elastomer sheets, at least one transverse edge 36, 38 is thinner. Thus, a difference in thickness on the one or more transverse edges of the sheet 26 is created, so as to create, after winding, a flared shape on one or both ends of the sleeve.

In addition, due to the presence of a prestressing force on an elastomer sheet and not on the other elastomer sheet, the area or the areas situated on the transverse edges having a single thickness will tend to deform. Thus, during winding, this or these areas will create the flared shape of one or both sleeve's ends shown in FIG. 5.

Because of the flared shape of the ends of the sleeve, the generation of virtual electrodes is suppressed. In addition, the flared end being flexible, such end will not damage the organ surrounded by the sleeve, in particular the organ close to the sleeve's ends.

According to a particular embodiment, the fixing step consists in fixing the elastomer sheet of lower width substantially centered on the width of the widest elastomer sheet.

In this way, a sleeve having two ends flared is created.

As illustrated in FIG. 11, in an alternative way, the elastomer sheet of smaller width can be positioned so as to create a sheet 26 providing a transverse edge having an area 73 of lower thickness with a higher thickness than the area of lower thickness on the second transverse edge 72. Thus, a sleeve having two flared ends is created, however, the height of the flared portion is higher than one of the ends relatively to the second end. To this end, the elastomer sheet of smaller width is positioned for example on the lower part of the width of the widest elastomer sheet. This embodiment is advantageous when the organ surrounded by the sleeve has, at one end of the sleeve, a large radius of curvature. In such a case, the flared shape of the sleeve's end makes it possible not to injure the organ by shearing.

The first elastomer sheet may be of lower width than the second elastomer sheet Thus, the elastomer sheet undergoing the pre-stretching is greater in width than the unstretched elastomer sheet. Conversely, the second elastomer sheet may be of smaller width than the first elastomer sheet. Thus, its elastomer sheet carrying the electrodes has a width smaller than the width of the elastomer sheet undergoing stretching.

The invention claimed is:

1. An implantable probe comprising;
   a sleeve adapted to be wound around an elongated cylindrical organ such as a nerve, the sleeve comprising;
      a sheet of elastically deformable material carrying at least one detection/stimulation electrode, the sheet being prestressed so as to allow its self-winding from an initial position where the sheet is held under stress in the deployed state to a final position where the sheet is freely spirally wound forming the sleeve around the organ,
      the sheet being delimited by an outer lateral edge of the sleeve after winding, an inner lateral edge of the sleeve after winding, a first transverse edge joining the first homologous ends of the outer lateral edge and the inner lateral edge, and a second opposite transverse edge joining homologous second ends of the outer lateral edge and the inner lateral edge,
      wherein in the final position of the sleeve, the sheet comprises at least one area having a constraining force near the first and/or second transverse edge on the longitudinal edges lower than the constraining force of an area located in a middle region of the sheet so as to create a flare on at least one end of the sheet.

2. The implantable probe according to claim 1, wherein the area having a smaller constraining force is localized in at least one area extending up to 50% of the width of the sheet near the first and/or second transverse edge, the width of the sheet being defined by the distance between the first and the second transverse edge.

3. The implantable probe according to claim 1, wherein the lower constraining force area exhibits a decreasing constraining force gradient across the width of the area extending from the inside of the sleeve towards the transverse edge of the sleeve.

4. The implantable probe according to claim 1, wherein the area having a lower constraining force is formed of an elastomer sheet and the area in the middle area comprises at least two elastomer sheets.

5. A manufacturing method of a sleeve for an implantable probe, adapted to be wound around an elongated cylindrical organ such as a nerve, the sleeve comprising a sheet of elastically deformable material carrying at least one detection/stimulation electrode, the sheet being prestressed so as to allow its self-winding from an initial position where the sheet is held under stress in the deployed state to a final position where the sheet is freely spirally wound to form the sleeve around the organ,
   the sheet configured to create a flare on at least one end of the sleeve in the final position,
   the sheet being delimited by an outer lateral edge of the sleeve after winding, an inner lateral edge of the sleeve after winding, and a first transverse edge joining first homologous ends to the outer lateral edge and the inner lateral edge, and a second opposite transverse edge joining second homologous ends of the outer lateral edge and the inner lateral edge,
   the sheet being formed of at least a first and a second elastomer sheet,
   wherein the method comprises:
      stretching the second elastomer sheet in a direction that is perpendicular to the winding axis of the sheet, a lower stretching being performed in an area near the first and/or second transverse edge on the longitudinal edges with respect to a prestressed area in a middle region of the sheet; and fixing the second elastomer sheet stretched over the first elastomer sheet.

6. The method according to claim 5, wherein the area having a lower constraining force is localized in at least one area extending up to 30% of the width of the elastomer sheet near the first and/or second transverse edge, the width of the elastomer sheet being defined by the distance between the first and the second transverse edge of the sheet.

7. The method according to claim 5, wherein the lower constraining force region exhibits a decreasing constraining force gradient across the width of the area, extending from the end of the area closest to the middle part of the elastomer sheet to the transverse edge of the lower prestressed area.

8. A manufacturing method of a sleeve for an implantable probe, adapted to be wound around an elongated cylindrical organ such as a nerve, the sleeve comprising a sheet of elastically deformable material carrying at least one detection/stimulation electrode, the sheet being prestressed so as to allow its self-winding from an initial position where the sheet is held under stress in the deployed state to a final position where the sheet is freely spirally wound to form the sleeve around the organ,
- the sheet configured to create a flare on at least one end of the sleeve in the final position,
- the sheet being delimited by an outer lateral edge of the sleeve after winding, an inner lateral edge of the sleeve after winding, and a first transverse edge joining first homologous ends to the outer lateral edge and the inner lateral edge, and a second opposite transverse edge joining second homologous ends of the outer lateral edge and the inner lateral edge,
- the sheet being formed of at least a first and a second elastomer sheet,
- wherein the method comprises:
  - stretching the second elastomer sheet in a direction that is perpendicular to the winding axis of the sheet,
  - fixing the second elastomer sheet stretched over the first elastomer sheet, wherein the first elastomer sheet and the second elastomer sheet are different widths, the width being defined by the distance between the lateral edges of said elastomer sheets.

9. The method according to claim 8, wherein fixing the second elastomer sheet stretched over the first elastomer sheet comprises fixing the elastomer sheet of smaller width substantially centered over the width of the widest elastomer sheet.

10. The method according to claim 8, wherein the first or second elastomer sheet of smaller width has a width between 60 and 80% of the width of the first or second elastomer sheet of greater width.

11. The method according to claim 8, wherein the width of the first elastomer sheet is less than the width of the second elastomer sheet.

12. The method according to claim 8, wherein the width of the second elastomer sheet is less than the width of the first elastomer sheet.

* * * * *